United States Patent [19]

Hon et al.

[11] Patent Number: 4,860,768
[45] Date of Patent: Aug. 29, 1989

[54] TRANSDUCER SUPPORT BASE WITH A DEPENDING ANNULAR ISOLATION RING

[75] Inventors: Edward H. Hon, Bradbury; Edward D. Hon, San Francisco; Robert W. Hon, Los Altos, all of Calif.

[73] Assignee: The Hon Group, Encino, Calif.

[21] Appl. No.: 163,859

[22] Filed: Mar. 3, 1988

Related U.S. Application Data

[63] Continuation-in-part of Ser. No. 118,441, Nov. 9, 1987, which is a continuation-in-part of Ser. No. 915,130, Oct. 2, 1986.

[51] Int. Cl.⁴ .............................................. A61B 5/10
[52] U.S. Cl. .................................... 128/778; 128/775
[58] Field of Search ............................... 128/660–663, 128/639–641, 643–644, 774–775, 778, 780, 782, 798, 802–803, 672, 691, 662.03–662.04

[56] References Cited

U.S. PATENT DOCUMENTS 4,355,643 10/1982 Laughlin et al. .................... 128/663
4,556,066 12/1985 Semrow .......................... 128/663 X
4,712,428 12/1987 Ishii et al. ............................ 73/644

FOREIGN PATENT DOCUMENTS 0919658 4/1982 U.S.S.R. .

Primary Examiner—Kyle L. Howell
Assistant Examiner—Angela D. Sykes
Attorney, Agent, or Firm—Lewis Anten

[57] ABSTRACT

An improved support base for supporting a transducer used for the monitoring of uterine contractions is disclosed. A support plate is concave and has a projecting annular ring on its lower surface spaced from and surrounding the central opening in the support plate, which acts as an isolation ring and to deform the skin into a hemispherical shape for being brought into contact with the transducer.

12 Claims, 1 Drawing Sheet

TRANSDUCER SUPPORT BASE WITH A DEPENDING ANNULAR ISOLATION RING

RELATED APPLICATIONS

This is a continuation-in-part of copending application Ser. No. 118,441, IMPROVED SENSOR SUPPORT BASE AND METHOD OF APPLICATION, which was a continuation in part of application Ser. No. 915,130, UTERINE CONTRACTION MEASURING DEVICE, both pending.

BACKGROUND

Previously, in order to hold an external pressure transducer in place to effectively monitor the uterine contractions of a pregnant patient, it was necessary to use a flexible belt wrapped around the body of the patient. This is commonly referred to as a tocodynamometer or toco belt. Such a toco belt is easy to apply, but not easy to use, and further, it is not possible for the toco belt to maintain the transducer in a stable position. Movement of the patient, even such mild movement as the patient rolling over in bed, will result in the loss of reliability of the signal of the transducer. Walking or exercising is not possible at all without loss of the signal.

The applicant has used an adhesively applied transducer support base that permits the transducer to be fixed directly to the patient so that reliable data can be obtained, even with vigorous movement by the patient, such as during walking and exercising.

In copending application Ser. No. 915,130 the use of a substantially concave support base having a central hollow tubular member was disclosed. The support base was adhesively attached to the patient and the transducer fitted into the hollow tubular member and was held against the abdomen by pressure applied by a cap.

Such a device was found to work reliably, but had limited value on very obese patients. With obese patients, this device required a special support plate that had a hollow tubular member that could be adjusted so as to press downwardly into the abdomen of the heavy patient, so that the transducer could obtain reliable measurements of the contractions. However, the pressure of the extended hollow tubular member against the abdomen was uncomfortable, particularly if the device was used for a substantial length of time.

In copending patent application Ser. No. 118,441 a series of struts was devised connecting the hollow tubular member to a flexible support plate. This modification permits one basic support plate to be used on different sized patients. The struts serve to effectively lower the central portion of the hollow tubular member in relationship to the perimeter of the flexible support plate, thereby causing the perimeter of the hard area of the support plate to form, in effect, an isolation ring which caused increased tension in the confined cutaneous tissue. Such a device, however, is not as simple to use as a device with no adjustable parts, and also is more expensive to manufacture.

OBJECTS OF THE INVENTION

It is an object of the present invention to provide an improved transducer support base that can be used on a wide range of patients.

It is another object of the present invention to provide an improved transducer support base that is simple to use.

It is still another object of the present invention to provide an improved transducer support base that is reliable.

It is yet another object of the present invention to provide an improved transducer support base that can be easily and inexpensively manufactured.

It is another object of the present invention to provide a support base for a pressure transducer that permits obtaining better data.

These and other objects and advantages of the present invention will be apparent from a reading of the following specification and the accompanying drawings.

SUMMARY OF THE INVENTION

The present invention comprises a transducer support base comprising a substantially concave support plate and an upstanding hollow tubular member for receiving and supporting a pressure transducer attached to the center of the support plate. The support plate has a relatively rigid inner portion made of a material such as hard plastic and an outer portion made of a relatively flexible material such as soft rubber.

An annular isolation ring of relatively rigid material extends from the lower surface of the support plate proximate the point where the flexible outer portion joins the relatively rigid inner portion. Adhesive is applied only to the lower surface of the flexible outer portions to attach the support base to the patient. A series of openings may be provided in the relatively rigid inner portion to assist in the removal of the support base after use. Absorbent material may also be used on a portion of the relatively rigid inner portion to absorb perspiration from the patient, thereby preventing any moisture from coming into contact with the adhesive and weakening the adhesive bond to the patient.

DETAILED DESCRIPTION OF THE INVENTION

Figure 1:
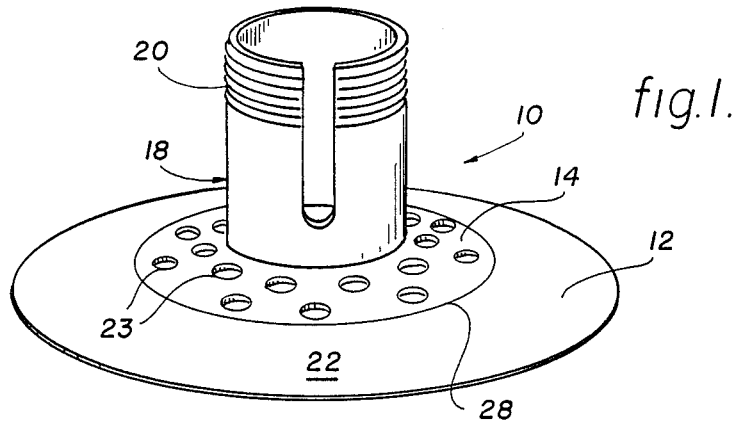
FIG. 1 is a top perspective view of the present invention.
Figure 2:
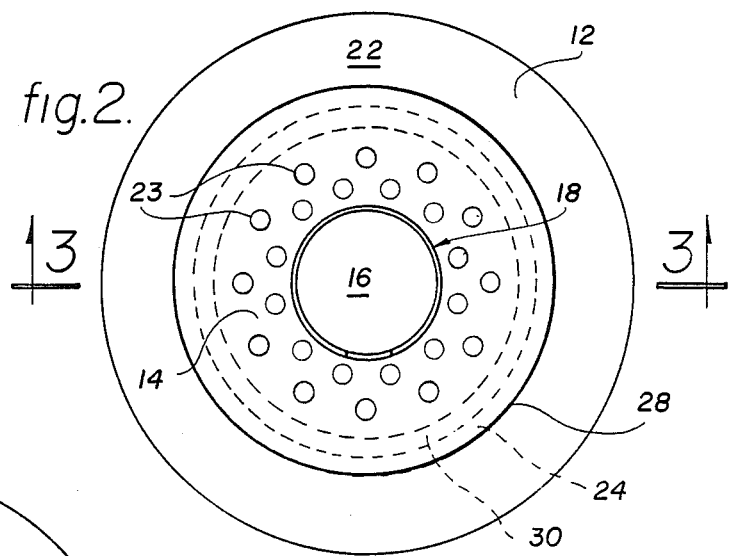
FIG. 2 is a top view of the present invention.
Figure 4:
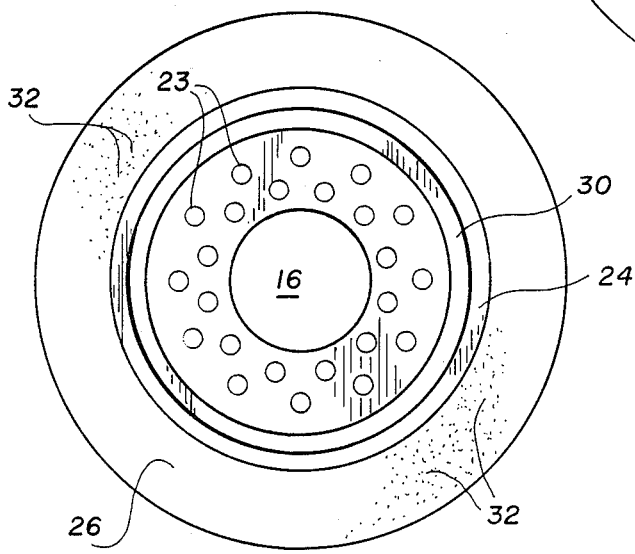
FIG. 4 is a bottom view of the present invention.
Figure 3:
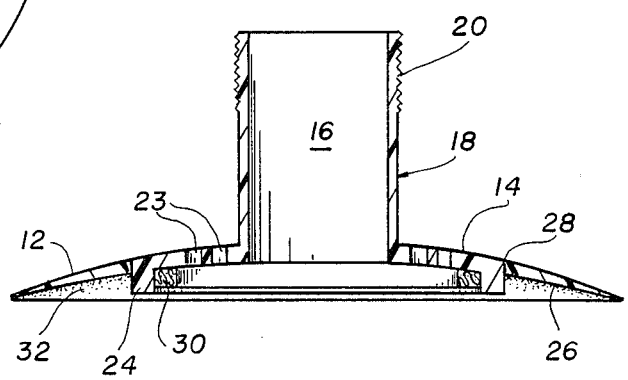
FIG. 3 is a side sectional view of the device taken along lines 3—3 of FIG. 2.

Referring to the drawings, the transducer support base 10 of the present invention is shown. The support base 10 consists of a concave support plate 12 having a relatively rigid inner portion 14 and a relatively flexible outer portion 22. A rigid hollow tubular member 18 is formed integrally with the rigid inner portion 14 and extends from the top surface of the support plate 12 forming a central opening 16. The top portion of the hollow tubular member 18 is threaded 20 so as to receive a complimentary cap (not shown).

The relatively flexible outer portion 22 is, in the preferred embodiment, made of a soft plastic and the relatively rigid outer member 14 is made of hard plastic.

The relatively flexible outer portion 22 is approximately one inch wide and has an outer diameter of about 5 inches and an inner diameter of about 3 inches. The relatively rigid inner portion 14 of the support plate 12 is approximately three inches in diameter, and the inner central opening is approximately one inch in diameter.

A series of small openings 23 are formed in the relatively rigid inner 14 portion of the support plate 12 to permit a solvent to pass into the bottom of the support and thus facilitate the removal of the support base 10 after use.

An annular depending ring 24 is located on the lower surface 26 of the support plate 12, proximate the juncture 28 of the relatively rigid inner portion 14 and relatively flexible outer portion 22 and substantially surrounds the circumference of the relatively rigid inner portion 14. The annular ring 24 is approximately ¼ inch wide, approximately ⅛ inch in depth and has an inner diameter of about 2¼ inches and an outer diameter of approximately 2¾ inches. The annular ring 24 is made of a relatively rigid material such as hard plastic and is formed integrally with the relatively rigid inner portion 14.

An absorbent material 30 may be used in association with the support base 10, such absorbent material 30 being placed on the lower surface 26 on the side of the annular ring 24, towards the central opening 16. The absorbent material 30 serves to absorb any perspiration from the patient. The annular ring 24 alone may prevent some of the perspiration from coming into contact with the adhesive, but use of the absorbent material 30 may be desirable to insure that the adhesive is not adversely affected.

In the preferred embodiment, medical grade adhesive 32 is applied to the lower surface 26 of the relatively flexible outer portion 22 of the support plate 12. A removable protective paper backing (not shown) can be applied over the adhesive 32 until it is desired to use the support base 10. However, adhesive may be applied to the relatively flexible outer portion by application of double sided tape, or by means of an annular adhesive tape applied over the relatively rigid inner portion 14.

In use the support base is applied to the abdomen of the patient in the area to be monitored. This is achieved by removing the protective paper backing and then firmly pressing the support base 10 against the patient. The transducer is then inserted into the hollow tubular member 18 and held in place by a cap (not shown).

The depending annular ring 24 presses against the skin on the abdomen of the patient, causing a portion of the skin to deform into the space formed between the walls of the annular ring and the lower surface 26 of the support base, surrounded by the annular ring 24. This confined hemispherical section of skin is thereby largely isolated from the changes in skin tension associated with maternal abdominal wall movement. This approach to the measurement of uterine activity is contrary to the currently used guard-ring systems, where the tissue immediately surrounding the measuring transducer is "turned into a flat diaphragm" and the face of the transducer is in the exact same plane as the guard ring (See "The Guard Ring Tocodynamometer" Journal of Obstetrics and Gynecology 64:59–66, 1957.)

The current transducer support plate and annular ring system purposely distorts the tissue into a hemispherical section which isolates the tissue and increases the tension therein, presenting the transducer with a portion of tissue preconditioned for taking pressure measurements. The annular ring therefore complements the function of the isolation ring of the transducer itself, contemplated to be used with this device. This permits greater sensitivity in the measurement of uterine contractions.

The use of the annular ring 24 has been found to expand the range of patients that are able to use the same support base during monitoring of contractions while increasing the sensitivity of the measurements of the uterine contractions.

In the preferred embodiment, the width of the relatively flexible outer portion 22 and the relatively rigid inner portion 14 are both about two inches. The surface area of the adhesive contacting portion on the relatively flexible outer portion 22 must be such as to attach the support plate 12 to the patient sufficiently so as to withstand the lateral and vertical stresses placed on the support plate 12 during use. Making the relatively flexible outer portion 22 of the support plate 12 larger does not result in significant additional adhesion but only serves to increase the bulk of the unit. Making the inner relatively rigid portion 14 significantly smaller, reduces the stability of the device.

The dimensions of the annular ring 24 are such that it does not impinge upon the abdomen of the patient so as to become uncomfortable during long periods of use. In the preferred embodiment, the annular ring 24 is sufficiently spaced from the central opening 16 where the pressure transducer is pressing upon the patient. As long as the annular ring 24 serves to isolate and deform the skin into the space between the walls of the annular ring 24 and the lower surface 26 of the support plate 12, the desired results can be obtained. However, if the diameter is too large, then the deformation of the skin tissue into a hemispherical section will not be achieved.

While the invention has been described with regards to a preferred embodiment, it is possible that other variations and embodiments of the present invention can be devised without departing from the overall concept of the present invention. For example, the annular ring 24 can be used on a support plate that is entirely rigid, although it will not be as desirable or as easy to use.

What is claimed is:

1. A pressure transducer support base comprising a concave support plate having an upper and a lower surface, an opening in said pressure transducer base for receiving a transducer, and an isolating means for isolating the pressure transducer, said isolating means comprising a member depending from said lower surface substantially surrounding said opening.

2. The device of claim 1 in which said isolating means comprises an annular ring substantially surrounding a relatively rigid inner portion.

3. The device of claim 2, in which said support plate comprises the relatively rigid inner portion, said relatively rigid portion being annular and further being surrounded by a relatively flexible annular outer portion.

4. The device of claim 3 in which said annular ring is located approximately at the juncture of said inner annular portion and said outer annular portion.

5. The device of said claim 3 in which the width of relatively rigid inner annular portion is approximately the same width as the relatively flexible outer annular portion.

6. The device of claim 5 in which the diameter of the annular ring is approximately three inches.

7. The device of claim 1 in which said isolating means comprises an annular ring, said annular ring having a depth less than ½ inch.

8. The device of claim 1 in which said lower surface of said support plate has adhesive applied thereto.

9. The device of claim 1 including means associated with said support base for permitting the variable application of downward pressure to said transducer.

10. A support base for a pressure transducer comprising a concave support plate having a central opening therein including means for receiving and holding a pressure transducer; said support plate having a relatively flexible outer portion around the circumference of a relatively rigid inner portion; the width of the relatively rigid portion being approximately the same as the width of the relatively flexible outer portion; and in which said support plate has an upper and a lower surface, the lower surface of said support plate having a depending isolating ring affixed thereto, said depending isolating ring substantially surrounding said central opening.

11. The device of claim 1, including an absorbent material on said lower surface surrounding said central opening.

12. The method of using a pressure transducer support base comprising a concave support plate having an upper and a lower surface, an opening in said pressure transducer base for receiving a transucer, and an isolating means for isolating the pressure transducer, said isolating means comprising a member depending from said lower surface substantially surrounding said opening, in which said method comprises the steps of adhesively attaching the support base to the abdomen of the patient, inserting the pressure transucer and recording the variations in the pressure applied to said pressure transducer.

* * * * *